United States Patent
Wimberger-Friedl et al.

(10) Patent No.: US 8,987,684 B2
(45) Date of Patent: Mar. 24, 2015

(54) DETECTION SYSTEM AND METHOD

(75) Inventors: Reinhold Wimberger-Friedl, Eindhoven (NL); Marius Iosif Boamfa, Eindhoven (NL); Erik Martinus Hubertus Petrus Van Dijk, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 784 days.

(21) Appl. No.: 12/747,522

(22) PCT Filed: Dec. 10, 2008

(86) PCT No.: PCT/IB2008/055194
§ 371 (c)(1),
(2), (4) Date: Jun. 11, 2010

(87) PCT Pub. No.: WO2009/081305
PCT Pub. Date: Jul. 2, 2009

(65) Prior Publication Data
US 2010/0270478 A1 Oct. 28, 2010

(30) Foreign Application Priority Data

Dec. 19, 2007 (EP) .................................. 07123575

(51) Int. Cl.
*F21V 9/16* (2006.01)
*G01N 21/64* (2006.01)

(52) U.S. Cl.
CPC ................................ *G01N 21/6456* (2013.01)
USPC ................... 250/458.1; 250/459.1; 250/461.1

(58) Field of Classification Search
USPC ................................. 250/458.1, 459.1, 461.1
See application file for complete search history.

(56) References Cited

U.S. PATENT DOCUMENTS

| 5,091,652 A | 2/1992 | Mathies et al. |
| 6,015,674 A | 1/2000 | Woudenberg et al. |
| 6,066,245 A | 5/2000 | Trost |
| 7,076,092 B2 | 7/2006 | Hollars et al. |

(Continued)

FOREIGN PATENT DOCUMENTS

| JP | 2003057169 A | 2/2003 |
| JP | 2005043278 A * | 2/2005 |

(Continued)

OTHER PUBLICATIONS

Shotton, D. "Confocal Scanning Optical Microscopy and Its Applications for Biological Specimens"; Journal of Cell Science, vol. 94, 2006, pp. 175-206.

(Continued)

*Primary Examiner* — Christine Sung (57) ABSTRACT

A detection system, comprising: a radiation source (24) for providing input radiation; a radiation focusing arrangement (26) for providing the input radiation to an analysis region of a sample (20);—a radiation collection (26) arrangement for collecting output radiation from the analysis region of the sample resulting from interaction of the input radiation with the sample; a radiation detector (28) for detecting the collected output radiation; operating means (40,50,60) for operating the detection device in a first detection mode and a second detection mode, wherein in the first detection mode the analysis has a first size and/or shape and wherein in the second detection mode the analysis region has a second size and/or shape that is different from the first size and/or shape.

18 Claims, 6 Drawing Sheets

(56) References Cited

U.S. PATENT DOCUMENTS

| | | | |
|---|---|---|---|
| 7,335,898 B2* | 2/2008 | Donders et al. | 250/458.1 |
| 7,609,391 B2* | 10/2009 | Betzig | 356/521 |
| 2002/0051974 A1 | 5/2002 | Dodge et al. | |
| 2003/0223059 A1 | 12/2003 | Li | |
| 2006/0006067 A1 | 1/2006 | Unger | |
| 2006/0147176 A1* | 7/2006 | Takamatsu et al. | 385/147 |
| 2007/0098594 A1 | 5/2007 | Elkin et al. | |
| 2007/0206192 A1* | 9/2007 | Fomitchov et al. | 356/416 |
| 2009/0066934 A1* | 3/2009 | Gao et al. | 356/73 |
| 2009/0296207 A1* | 12/2009 | Goelles et al. | 359/385 |

FOREIGN PATENT DOCUMENTS

| | | |
|---|---|---|
| WO | 9940416 A1 | 8/1999 |
| WO | 2004104547 A2 | 12/2004 |
| WO | 2005010494 A2 | 2/2005 |
| WO | 2006031537 A2 | 3/2006 |
| WO | 2006098752 A2 | 9/2006 |
| WO | 2006107627 A1 | 10/2006 |
| WO | 2006128321 A1 | 12/2006 |
| WO | 2007063457 A2 | 6/2007 |

OTHER PUBLICATIONS

Roth, C.:"Quantifying Gene Expression"; Current Issues in Molecular Biology, vol. 4, 2002, pp. 93-100.

Ploton et al: "Three-Dimensional Co-Localization of Nucleolar Argyrophilic Components and DNA in Cell Nuclei by Confocal Microscopy"; The Journal of Histochemistry and Cytochemistry, vol. 42, No. 2, 1994, pp. 137-148.

Demidov, V.: "10 Years of Rolling the Minicircles: RCA Assays in DNA Dagnostics"; Expert Review of Molecular Diagnostics, Future Drugs Ltd, 2005, pp. 477-478.

\* cited by examiner

DETECTION SYSTEM AND METHOD

FIELD OF THE INVENTION

The invention relates to a detection system and a detection method for detecting output radiation from a sample. The invention also relates to a computer program product enabling a programmable device for executing the detection method and a controller for controlling a detection system to perform the steps of the detection method.

BACKGROUND OF THE INVENTION

One example of a detection system is based on excitation of a sample in order for it to induce fluorescence that is detected to analyze the sample. The example has been used in nucleic acid testing (NAT). This is a core element in molecular diagnostics for detecting genetic predispositions for diseases, for determining RNA expression levels or identification of pathogens, like bacteria and viruses that cause infections.

In many cases, particularly in the identification of pathogens, the amount of target DNA present in a reasonable sample volume is very low, and this does not allow direct detection. Amplification techniques are necessary to obtain detectable quantities of the target material. Different amplification techniques have been proposed and are used in daily practice. The most widely used are based on the so-called Polymerase chain reaction (PCR).

The amplification involves the denaturing of double-stranded DNA at elevated temperature (typically >90 degrees Celsius), specific binding of primers to the DNA sample at a reduced temperature (approximately 65 degrees) and copying of the original sequences starting from the primer position (at approximately 70 degrees). This procedure is repeated and in every cycle the amount of DNA with the specific sequence is doubled (when proceeding at 100% efficiency).

After amplification, the presence of target DNA is detected by measuring the fluorescence intensity of the labeled amplified DNA at the end-point, for instance after electrophoretic separation in a capillary or after hybridization to so-called capture probes which are applied in spots on a surface over which the amplification product is flowed. Such methods are referred to as end-point PCR detection methods. These methods in general do not allow a quantitative determination of the initial concentration of a particular DNA sequence, but rather a qualitative answer of whether a certain target sequence was present in the sample or not.

For a quantitative determination of the concentration of target DNA the so-called quantitative (q-PCR) or real-time PCR technique is available. q-PCR is based on the general method of PCR amplification but it allows monitoring the DNA concentration dynamically, at the end of every amplification cycle. This is based on special fluorescent probes that luminescence only when hybridized to the amplified DNA product.

Figure 1A:
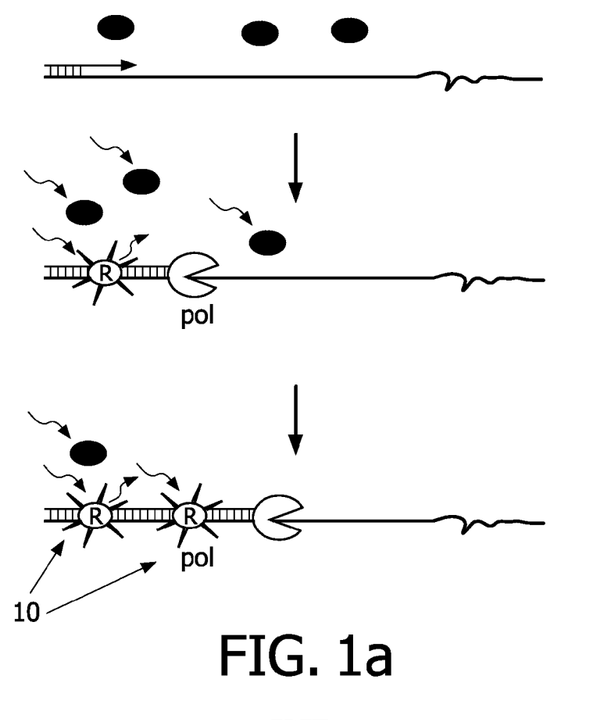
FIGS. 1a and 1b show schematically two techniques for generating fluorescence during DNA replication in a quantitative PCR technique.
Figure 1B:
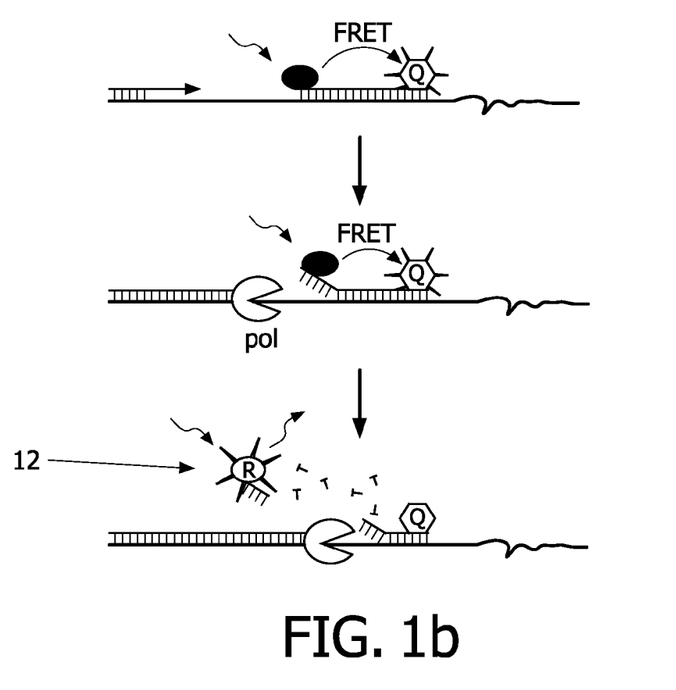

Different approaches are known, and two are shown schematically in FIG. 1. In FIG. 1a, the CBRgreen fluorophore as represented by the circles are quenched, i.e. they do not fluoresce if not incorporated into a double-stranded DNA molecule. They become fluorescent when bound to a double-stranded DNA, as shown at 10. With increasing concentration of double-stranded DNA after every cycle of the PCR, the fluorescence signal will increase and must be measured to analyze the replication situation.

An alternative approach uses the so-called Taq Man probe shown schematically in FIG. 1b. This approach is bound to a specific sequence of single-stranded DNA after denaturing. In this state, energy transfer to an adjacent dye quenches the fluorophore. When the sequence is replicated starting from the primer, the probe is chopped and removed from the template as schematically shown. The amount of fluorescent signal is proportional to the amount of released probe 12 that is proportional to the number of DNA molecules.

Several alternative probe techniques have been developed with similar characteristics.

It will be apparent from the introduction, that the detection of fluorescence is required both for a qualitative determination of the presence of a particular target DNA sample, and for a quantitative determination of the amount of DNA present in a sample.

SUMMARY OF THE INVENTION

It is an object of the invention to provide a detection system and a detection method which are able to fulfill the above requirements.

The invention is defined by the independent claims. The dependent claims define advantageous embodiments.

According to the invention, there is provided a detection system and a detection method for detecting output radiation from an analysis region of a sample wherein the size of the analysis region can be varied between different detection modes of operation by an operating means with which the analysis region (or equivalently a radiation input region) can be changed by changing the system on the radiation input side of the system.

The input radiation may be provided by focusing. A diffraction limited spot can be used in at least one of the detection modes.

Within the context of the invention, the analysis region is to be construed as an analysis volume with an analysis volume shape. The analysis volume may be defined in a Cartesian coordinate system of which the z-axis is oriented in the direction perpendicular to the surface of the sample. The x- and y-axes then span a xy-plane perpendicular to the direction of the z-axis. The intersection of the beam of output radiation evolving from the sample with the xy-plane having some chosen z-coordinate and which is comprised within the sample defines a cross section of the analysis volume and accordingly defines an analysis area. Analysis areas at different z-coordinate within the analysis volume may very in size and/or shape.

The analysis region and thus the analysis volume or analysis area may have different sizes and/or shapes depending on the construction of the collection arrangement, the focusing arrangement or both. For example, if the focusing arrangement defines a focusing region, also to be construed as a focusing volume, that is entirely contained within the analysis region, i.e. that overlaps entirely with the analysis region then the collection arrangement defines the analysis region.

Thus an analysis area may be circular, oval, or elongated in the shape of a line. These may have their advantages as elucidated in the description hereinafter. The thickness of the analysis volume is typically measured along the z-axis. With the system and method of the invention it is possible to obtain from a sample qualitative information with the first detection mode and quantitative information with the second detection mode or vice versa. For example, the system offers the possibility to vary the analysis regions such that with the first mode surface directed detection is enabled while with the second detection mode volume directed detection is possible. Alternatively, or additionally in the different detection modes different analysis regions in terms of their projected analysis region area on a sample surface or in terms of different analysis region shape may be provided.

This different detection modes may for example be used to advantage in sensor or diagnostic systems based on oligo-, or polynucleotide determination using for example PCR, since the invention enables combined implementation of both end-point detection by one detection mode and real time PCR measurement by another detection mode.

The system and method may also be used for RCA or NASBA Procedures.

Providing the detection system with variation means for varying the size and/or shape of the analysis region allows that the detection system can be operated in at least two different detection modes. The first detection mode has an analysis region with a first size and the second detection mode has an analysis region with a second size that is different from the first size. With one of the detection modes qualitative sample information is obtained while with the other mode quantitative sample information is obtained.

Depending on the properties of the sample, the variation of the size of the analysis region may be effectuated as a variation in substantially analysis area without substantially altering the analysis area thickness, or vice versa or both. Each having its advantages as elucidated hereinafter.

In the invention the analysis region is altered on the input radiation side of the system or the step of the method in which input radiation is provided. As a consequence, the detection device is arranged for detecting output radiation that result from interaction of the input radiation with the sample to generate the output radiation. To this end, in an embodiment the radiation collection arrangement is for example arranged to collect output radiation that results from input radiation scattered, reflected and/or transmitted by the sample. In this embodiment the frequency range of the input radiation is substantially the same as the frequency range of the output radiation. In another preferred embodiment, the radiation collection arrangement is arranged to collect output radiation in the form of luminescence radiation, which includes fluorescence and phosphorescence radiation. In this embodiment the input radiation is excitation radiation exciting the sample and resulting in the luminescent radiation to be emitted from the sample. In general the frequency range of the output radiation being the luminescence radiation is in general different from the frequency range of the input radiation being the excitation radiation.

The detection system may be an optical detection system and the radiation collection arrangement arranged to detect radiation for example from the UV and/or visible spectrum.

The detection system is suitable as a characterization or analysis system for examination of chemical, biological and/or biochemical samples. The samples may be solid, liquid and/or gaseous. They may be substantially pure substances and/or homogeneous or heterogeneous mixtures.

The detection system is advantageous if in one mode a constitution of a sample needs to be determined only once while in the other detection mode the variation or changes of the constitution of the sample during time especially in view of evolving chemical reactions within the sample needs to be measured.

Of particular interest is the application of the invention in the field of biosensing or diagnostics. It allows a flexible, scalable and cost effective approach for analysis of samples with respect to qualitative and quantitative constitution. In the chemical or biochemical applications samples may be solutions comprising one or more constituents to be detected. The detection system and method may be adapted to characterize blood, saliva or other bodily fluids either pure or prepared in any way with respect to constituents also referred to as targets or analytes such as for example: viruses, bacteria, microbes, proteins, enzymes, hormones or other regulatory species, oligo- or polynucleotides such as for example RNA and DNA sequences or drugs or medication.

The system can for example comprise a oligo-, or polynucleotide replication apparatus, such as a polymerase chain reaction apparatus, hereinafter "PCR", apparatus. In this case, based on the surface and bulk scanning modes, the detection system may be, but need not be operable in at least two modes a first detection mode for qualitative or end-point PCR, in which the analysis region has a first size and the system is confocal; and a second detection mode, in which the analysis region has a second, larger, size for providing the quantitative or real-time PCR detection.

The PCR apparatus may thus advantageously provide a qualitative investigation of oligo- or polynucleotides, i.e. with respect to their identification or properties and it may provide quantitative determine of the oligo-, or polynucleotide concentration inside for example the amplification chamber of the PCR apparatus.

Other replication apparatuses include those based on Rolling Circle amplification (RCA) as for example explained in the article published in Expert Rev. Mol. Diagn. 5(4), 2005, pages 477-478 and Nucleic Acid Sequence Based Amplification (NASBA).

Thus, the system allows both techniques (of qualitative and quantitative analysis) to be carried out in a flexible and cost efficient way, without redesign of the detection system equipment.

In an embodiment the invention can be based on multicolor radiation detection such as for example multiple luminescence detection enabling multiplexed determination of two or more different constituents within a sample. Multiplexing typically saves time due to simultaneous detections. This is especially so when the detection is also simultaneous using for example imaging detection as elucidate hereinafter.

In an embodiment the option of sample scanning in either one or a combination of the independent Cartesian coordinates is enabled. To this end the detection system may comprise a scanning radiation pick-up unit that comprises at least the radiation collection arrangement.

In an embodiment, the variation means are adapted to provide the analysis region with a first analysis area in the first mode and a second analysis area larger than the first analysis area in the second mode. This embodiment is advantageous in case that the properties of a sample are such that the measurement of quantitative sample information requires a larger analysis area than the measurement of qualitative data. Such may be determined by sample constituent concentration, sample constituent kinetic or thermodynamic properties. For example, measurement of output radiation from a analysis area of an immobilization surface in contact with a solution of to be detected constituents may not reflect the true concentration of the to be detected constituents in solution when immobilized on the immobilization surface when the size of the analysis area is small beyond a certain threshold value.

In an embodiment the detection system is a confocal detection system in at least one of the first and second detection modes. Thereto the radiation detection arrangement comprises a confocal imaging element, such as for example a refractive imaging element in the form of a lens in combination with an aperture onto which the confocal imaging element focuses the output radiation. The aperture may be arranged as a pinhole in the output radiation path before the detector. Alternatively, the aperture may be a pixel of a detector. In case that confocality is only to be provided in one of the detection modes, the confocal imaging element is preferably arranged such that its function is removed in the detection mode that does not require the confocal property. This may for example be done by removing the aperture or the aperture and the confocal imaging element from the radiation path in that non-confocal mode. The confocal detection may for example be provided to at least the first detection mode. Confocal detection is advantageous for a detection mode that is arranged for surface detection as it substantially filters out any output radiation that travels in a direction towards the radiation collection arrangement that does not coincide with a direction that is focused on the aperture. Hence confocality greatly reduces detection of radiation stemming from a sample location other than that which is placed in the focal point of the radiation detection arrangement. Background radiation form above and below an analysis region within a focal point is thus greatly reduced. It is advantageously used for the diagnostic systems that are arranged to follow chemical reactions in time such as the replication processes. have replication as described here before.

The latter option may provide switching between confocality and volume scanning. Furthermore, the unit can switch between operation in a confocal surface scanning mode as preferred for detection of surface bound or immobilized analytes of a sample and a non-confocal bulk scanning mode as preferred for volumetric inspection of a sample. The switching between modes providing improved versatility of the detection system is enabled by the adjustment of the confocality as defined for the invention.

In the general detection system of the invention and in particular the qualitative mode described here before, the first size can correspond to the diffraction limited spot created by the focusing arrangement (for example of the order of 1 cubic micron), whereas the second size is much larger, for example at least 10, at least 100, at least 500 or at least 1000 cubic microns.

The detection system may comprise a refractive element such as for example a lens that is shared by the radiation focusing arrangement and the radiation collection arrangement and which is arranged for providing input radiation to the sample and collecting output radiation from the sample. Preferably the input radiation is excitation radiation while the output radiation is luminescence radiation so that the refractive element is a shared excitation/collection element. This provides easy separation of both types of radiation on frequency properties.

The refractive element is preferably scannable to implement 3D scanning of a sample, as is known in confocal microscopy. For example, scanning in the independent Cartesian coordinates may be provided.

The means for varying the size of the analysis region can comprise means for altering the focal depth of the radiation focusing arrangement. This can change the focus from a spot to a volume, by providing a backward shifted focus. A collimating refractive element such as a lens can be used for collimating the output of the radiation source, and the size of the analysis region can then be varied by moving the collimating refractive element relative to the radiation source.

The means for varying the size of the analysis region can instead comprise means for introducing aberration into the path between the radiation source and the analysis region. This deliberate aberration can again increase the volume at the analysis region, i.e. at the focal point. The means for introducing aberration include for example a beam shaping phase plate. The aberration may be optical aberration depending on the radiation source used for the detection system.

In an embodiment the means for varying the size of the analysis region comprises an optical fiber which is insertable into the radiation path between the radiation source and the analysis region. This can provide a uniform light intensity across an area, and this can in turn limit the smallest size or area of the focal point which the system is able to generate on the sample.

In an embodiment the means for varying the size of the analysis region comprises a scattering element or medium which is insertable into the radiation path between the radiation source and the analysis region.

In an embodiment the detection system as comprising a refractive element that is shared by the radiation focusing arrangement and the radiation collection arrangement and is arranged for providing the input radiation to the sample and for collecting the output radiation from the sample. This embodiment is advantageous since system components are reduced by sharing thus reducing manufacturing cost and complexity as well as size of the system. In addition, if one of the detection modes is a surface detection mode either confocal or not where generally one needs to collect as much radiation as possible in a situation where the number of output generating species is reduced, a high numerical aperture refractive element can be used. However, such an element is not particularly suited as such for a volume measurement as the analysis region will be confined to a very small focal volume generally provided by such elements. The invention now enables the enlargement of the analysis region in the second detection mode without loosing the advantage of the use of the high numerical aperture in the first detection mode. Hence no replacement of refractive element is necessary. In addition one radiation detection path is necessary in the system.

The radiation detector may be chosen according to need. In one embodiment the radiation detector comprises spatially distributed pixels for detecting the radiation, i.e. it comprises a pixilated radiation detector. The amount and distribution of activated pixels can be appropriately chosen to switch between a small detection region for example for a surface detection mode and a large detection region for a volumetric detection mode. In an alternative embodiment, the radiation detector comprises a single detector surface, i.e. for example only one pixel of some necessary area, and the detection system may then further comprise an aperture member, such that the radiation detector is operable in a large area mode for a larger analysis region and in a small area mode for a smaller analysis region by using the aperture member. The radiation detector may for example be a charge coupled device (CCD) or a diode array detector.

Two different imaging lens arrangements can instead be used to enable the detector to be operable in the desired large area mode for a larger analysis region and the desired small area mode for a smaller analysis region.

With features corresponding to those of the system having corresponding advantages, the method of the invention may have the additional steps contained within process for oligo-, or polynucleotide replication such as for example PCR, RCA and/or NASBA. The input radiation may be provided by focusing a diffraction limited spot.

The method may comprise varying the size of the analysis region by altering the focal depth of a focusing arrangement which provides the input radiation to the analysis region of the sample.

The method may comprise the step of collimating an output of the radiation source using a collimating lens, and wherein varying the size of the analysis region comprises moving the collimating lens relative to the excitation radiation source.

The method may comprise the step of varying the size of the analysis region by introducing aberration into the input radiation path between the radiation source (24) and the analysis region.

According to the invention there is also provided a computer program product and a controller for controlling a detection system to perform the detection method of the invention. The computer program product may have the shape of an Integrated Circuit made by standard semiconductor technology such as contained within a computer.

BRIEF DESCRIPTION OF THE DRAWINGS

Examples of the invention will now be described in detail with reference to the accompanying drawings, in which.

DETAILED DESCRIPTION OF EMBODIMENTS

In particular, different amplification and detection methods can be employed with the same device. Typically, a sample will be stored on a disposable cartridge. The different modes can then be implemented by changing the size of the analysis region (i.e. changing the control settings of the system) and having different chemicals inserted in the cartridge.

Depending on the diagnostic scenario, it is required to detect a large number of different oligonucleotides in a qualitative or quantitative way. This requires multiplexed amplification, i.e. simultaneous amplification of different sequences. Multiplexing can be achieved by distributing the sample fluid (to be more precise the analytical solution which is obtained after sample pretreatment of DNA extraction and purification) over a multitude of chambers, each chamber containing a different set of primers targeting different sequences. Alternatively, the different primers can be combined in a single chamber and amplified next to each other. The latter obviously requires the absence of interference between different probes and target sequences.

Depending on the similarity of the different target sequences, a number of amplifications can be carried out in a single chamber. In the case of real time PCR there are additional limitations, as every sequence needs to be identified by a unique fluorophore characteristic and a unique probing sequence for selective hybridization. Therefore single chamber multiplexing is more limited in the case of real time PCR.

In addition, the very special reagents required make this method more expensive than end point (qualitative) detection for high degrees of multiplexing.

Molecular diagnostic devices based on the DNA amplification processes described above are currently based on different technologies that have different benefits depending on the number of sequences that need to be detected simultaneously.

It is desirable for a commercial device to be scalable and serve different applications requiring different degrees of multiplexing. For example, a diagnostic instrument should ideally be able to address different diagnostic questions, providing a platform approach. For small degrees of multiplexing, real time PCR is the preferred method and for larger degrees of multiplexing or very critical combinations of targets, endpoint detection is preferred.

The invention relates to a system which is capable of implementing different detection modes of detecting quantitative and qualitative properties of a sample. To achieve this, in the system (and method) of the invention, the detection of the luminescence (fluorescence) radiation can be switched between a (quasi-) confocal and a non-confocal arrangement.

Quantitative methods are known for the detection of the concentration of fluorophores in a device by exciting the fluorophores by light radiation through an objective lens and collecting the luminescence, for example through the same lens in a reflective mode. The luminescent radiation is projected onto a sensor device after having passed a filter device to select the appropriate wavelength range.

The lens can be moved in a controlled way in three directions by different actuation means, to enable scanning over a sample of interest. A non-confocal arrangement is desired for quantitative analysis, whereas a confocal arrangement is desired for end point analysis (i.e. for detection of the presence of a target).

Figure 2:
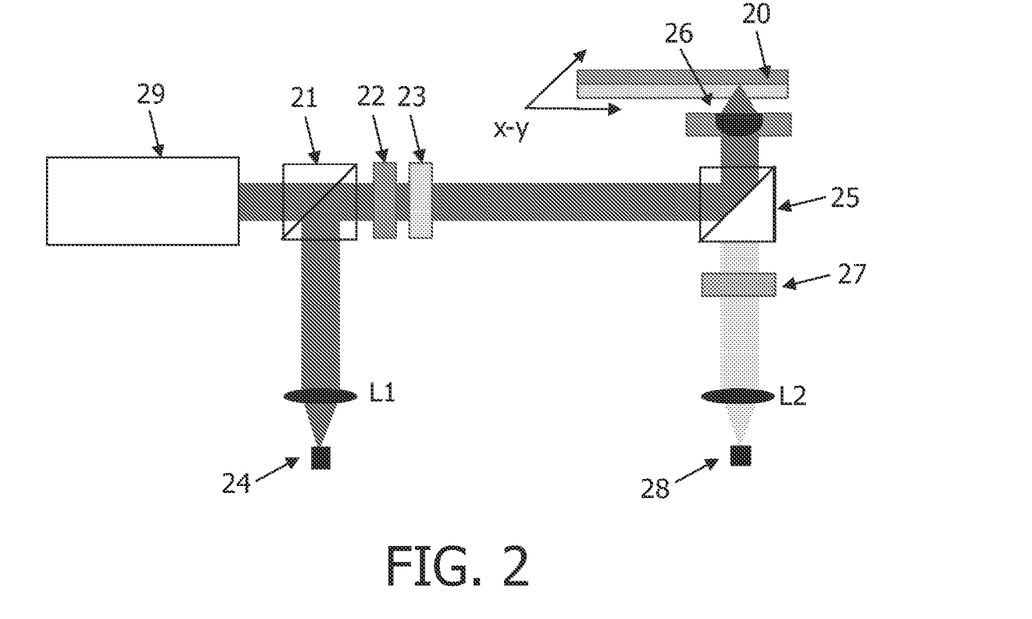
FIG. 2 shows a PCR apparatus of the invention.

FIG. 2 shows the basic components of a known fluorescence scanner based on a DVD optical system. The sample to be investigated is confined into a given volume within a substrate 20.

The light generated by a light source 24 such as a laser is used to excite fluorescence. The light is collimated by a collimator lens L1 and subsequently focused in the sample by means of an excitation lens 26.

The lens 26 can move relative to the sample, preferably in all three dimensions. This relative motion can be decoupled arbitrarily, for example the sample can move in to the x-y plane and the lens in the z direction. Alternatively, the sample can be kept fixed and the lens has all the three-degree of freedom (x-y-z) on its own. Any other arrangement is also possible.

The laser light is reflected by a polarization beam splitter 21, i.e. a polarization dependent reflector, and is passed through a quarter wave plate 22 and a first band pass filter 23.

A dichroic beam splitter 25, i.e. a wavelength dependent reflector, directs the laser light to the excitation lens 26.

The induced fluorescence, as a result of the excitation light focused into the sample, is collected by a collection lens, which in this example is the same component as the excitation lens 26, and is directed toward a detector 28.

Any reflected unabsorbed laser light is reflected again by the beam splitter 25, whereas the fluorescence is passed through the beam splitter 25. A second band pass filter 27 provides further filtering, and the light is then focused on the detector 28 by an imaging lens L2 which images the sample onto the detector 28.

Many different types of detector can be used such as a photon detector.

To the extent described above, the apparatus of FIG. 2 is conventional, and for this reason a detailed discussion of the optical components will not be given. The invention provides the ability to switch between confocal and non-confocal detection modes.

The confocal detection mode is the preferred method for endpoint detection (surface immobilization type of assay) while for real time PCR, volume detection may be appropriate.

In the confocal mode, the excitation volume is kept to a minimum, ideally to the diffraction limited spot that the excitation lens 26 can create. A typical confocal volume is in the order of a cubic micron, depending on the strength (numerical aperture, NA) of the excitation lens 26. The fluorescence created in this volume is collected by the collection lens and is imaged on the detector. In a confocal method, the focal point is confocal with a point in the detection path. At this point in the detection path, a small pinhole is typically placed to filter out any light coming from a location other than the focal point.

The light passing the pinhole is directed toward the detector. It is possible for the detector itself to play the role of the pinhole, with the restriction that the lateral size of the detector has to match the size of the focal point scaled by the numerical aperture of the imaging lens L2 divided by the numerical aperture of the collection lens 26.

This confocal mode is best suited to investigate a surface immobilization assay, as the result of an endpoint bio-experiment. The surface is scanned to analyze the full sample. On the contrary, in the case of real time PCR monitoring, a relatively large volume excitation and detection is desired. The reaction to be monitored is spatially distributed in a large volume and therefore confocal scanning is no longer a time effective option.

The excitation light needs to sample a larger, statistically relevant volume in the given time. This given time is a fraction of the PCR cycle corresponding to the time when the measurement of fluorescence provides the relevant information about the level of amplification. Ideally, a high efficiency of fluorescence collection is desired, with a high NA collection lens. There is a compromise between the lens performance and cost.

The detector arrangement is preferably designed so that the lens field of the imaging lens L2 matches the sampling volume. The detection lens field is the portion of the object plane that can be imaged by the lens in the object plane with minimum aberrations. As a consequence, the lateral dimensions of the detector are matched with the field of the collection lens 26, scaled with the NA ratio of the imaging lens 28 and collection lens 26. The excitation volume corresponds to this sampling volume.

A control arrangement 29 keeps the focus of the objective lens precisely at the inner surface of the analytical device which is in contact with the analyte, while scanning the same surface. The focus of the objective lens can also be offset on purpose.

By way of example, the volume defined by the lens field for an a-sphere singlet lens with a strength of numerical aperture of 0.6 is around 60×60×60 microns. Typically as the numerical aperture of the lens increases, the field of the lens decreases but this also depends on the particular lens design.

To switch optimally between the confocal and non-confocal modes of operation, both the excitation and detection path of the system needs to be modified.

Figure 3A:
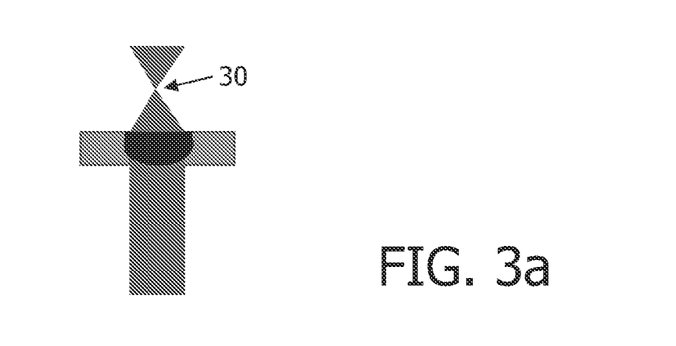
FIGS. 3a and 3b are used to explain a first way of changing a mode of operation of the apparatus of FIG. 2.
Figure 3B:
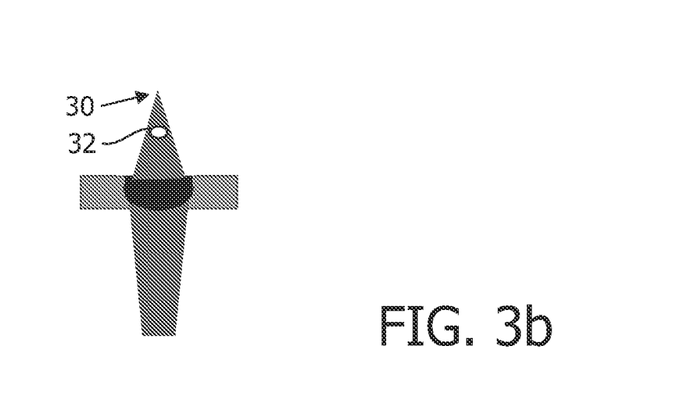

A first approach to the required expansion of the excitation volume is shown in FIG. 3, and provides backward shifting of the focal point 30 of the excitation lens. This can be achieved by modification of the plane-parallelism of the incoming (excitation light) wave front. The collimator lens, L1 in FIG. 2, can be used to achieve this result. Ideally the collimator lens L1 is placed at a distance equal to its focal length with respect to the laser. In this setting, the wave front of the excitation light (after passing the L1) is plane parallel as shown in FIG. 3a. A slight offset of the lens L1 from this position turns the excitation beam wave front into a divergent beam (when placing L1 further away) or a convergent beam (when placing L1 closer to the laser).

The effect of creating a divergent beam is shown in FIG. 3b, in which the focus 30 is backward shifted as the incoming light changes from plane parallel to divergent.

As the excitation light impinging on the excitation lens is divergent, the focus point 30 of the excitation light is backward shifted with respect to the situation when the excitation light was plane parallel. The excitation light is focused in a tight spot (before or after the focal plane of the excitation/collection lens 26), and care should be taken that this spot does not produce bleaching of the fluorophores in the PCR chamber. This can be ensured by providing horizontal scanning inside the chamber.

In this way, it is possible to excite reasonably uniformly a large volume 32 around the focal point of the excitation/collection lens.

Placing the collimator lens L1 on a motorized (mini-)stage enables easy switching between the two configurations. Alternatively, a tunable lens, such as an electrowetting lens, can be used to switch between different modes without mechanical actuation.

Figure 4A:
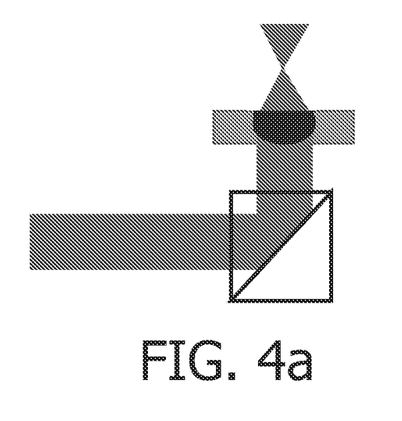
FIGS. 4a and 4b are is used to explain a second way of changing a mode of operation of the apparatus of FIG. 2.
Figure 4B:
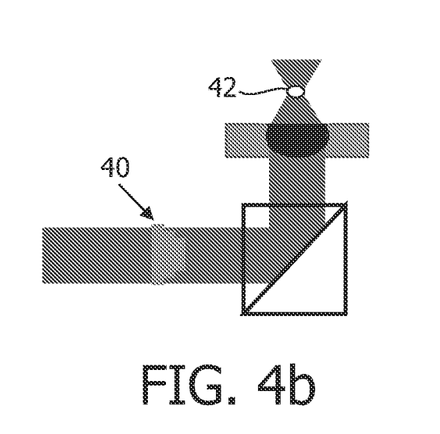

A second approach to the required expansion of the excitation volume is shown in FIG. 4, which shows how a phase plate 40 can introduce large aberrations in the beam thereby widening the focus spot.

The phase plate thus provides an alternative solution to switch between sharp focus excitation and wide focus excitations. The use of phase plates is widespread in multicolor systems, where typically a phase plate is used to shape the beam, to improve the wave front quality for all the colors used in the system. In this embodiment, on the contrary, the phase plate plays the opposite role, namely it introduces aberrations into the impinging wave front and as a consequence while focused by the excitation/collection lens the light would form a wide spot.

FIG. 4a shows the confocal arrangement with diffraction limited focus, and FIG. 4b shows the arrangement with larger aberration dominated focal volume 42.

When the confocal measurement mode is desired, the phase plate 40 is not present in the light path. For activating the large volume excitation, the phase plate 40 is placed in the beam path. The phase plate can also be a switchable phase plate which is switched on or tuned by electrical control. This can be more desirable than mechanically moving phase plates in and out of the light path.

Figure 5:
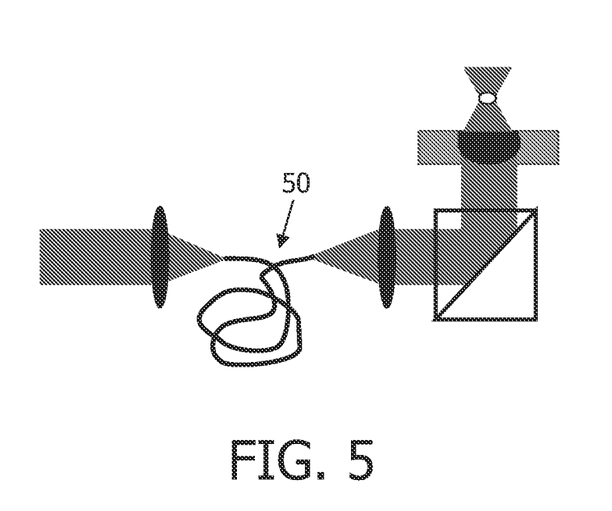
FIG. 5 is used to explain a third way of changing a mode of operation of the apparatus of FIG. 2.

A third approach to the required expansion of the excitation volume is shown in FIG. 5, which shows how an optical fiber 50 can be used for this purpose. The impinging light is coupled into a multimode fiber of a reasonable length. In the fiber 50, the incoming plane wave front is converted via mode conversion to the multitude of modes allowed to propagate in the fiber. The output of the fiber is collimated back and directed to the excitation lens.

Because of the mode conversion in the fiber, the light exiting the fiber is uniformly distributed over the fiber cross-section, and divergent within the NA of the fiber. As a consequence, the light cannot be focused by the excitation/collection lens into a spot that is smaller than the fiber diameter (scaled with the ratio of the two lenses NA). In this way, the size of the wide focus is controlled by the fiber diameter. The whole system, two lenses and fiber, preferably form a single block that can be place in/out the beam, switching the system between confocal and large volume excitation. In FIG. 5, the focal volume 52 is again aberration dominated.

Figure 6:
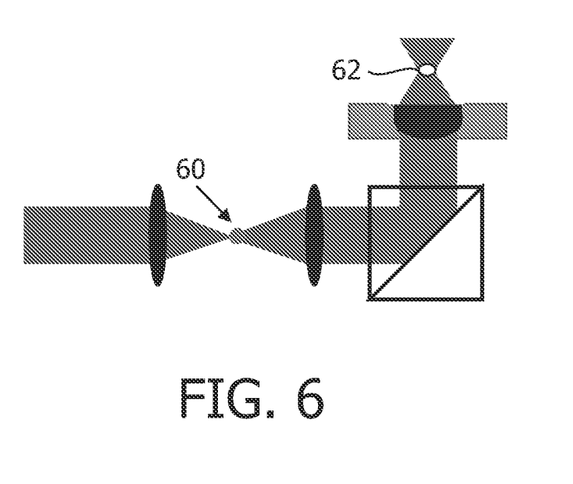
FIG. 6 is used to explain a fourth way of changing a mode of operation of the apparatus of FIG. 2.

A fourth approach to the required expansion of the excitation volume is shown in FIG. 6, which shows how a scattering media 60 can be used for this purpose. This approach again alters the quality of the wave front, with the direct consequence of enlarging the focal spot. As light is focused on a scattering media the light is diffused (re-distributed) in the scattering media and as the front propagates through the scattering media the size of the spot is increased. A predominantly forward scattering media is preferred, so the losses of light scattered out of the useful optical path are minimal. The size of the focal spot 62 created by the excitation/collection lens can be tuned by the scattering media thickness or scattering medium properties (scattering efficiency).

Electrically actuated tunable diffusers, like LC-gels or PDLC's can be used for this purpose. Placing the scattering media in or out of the beam or switching it on or off switches the system operation mode between large area excitation and tight focus spot excitation.

The detection system needs to be able to operate correctly in the two modes.

Figure 7:
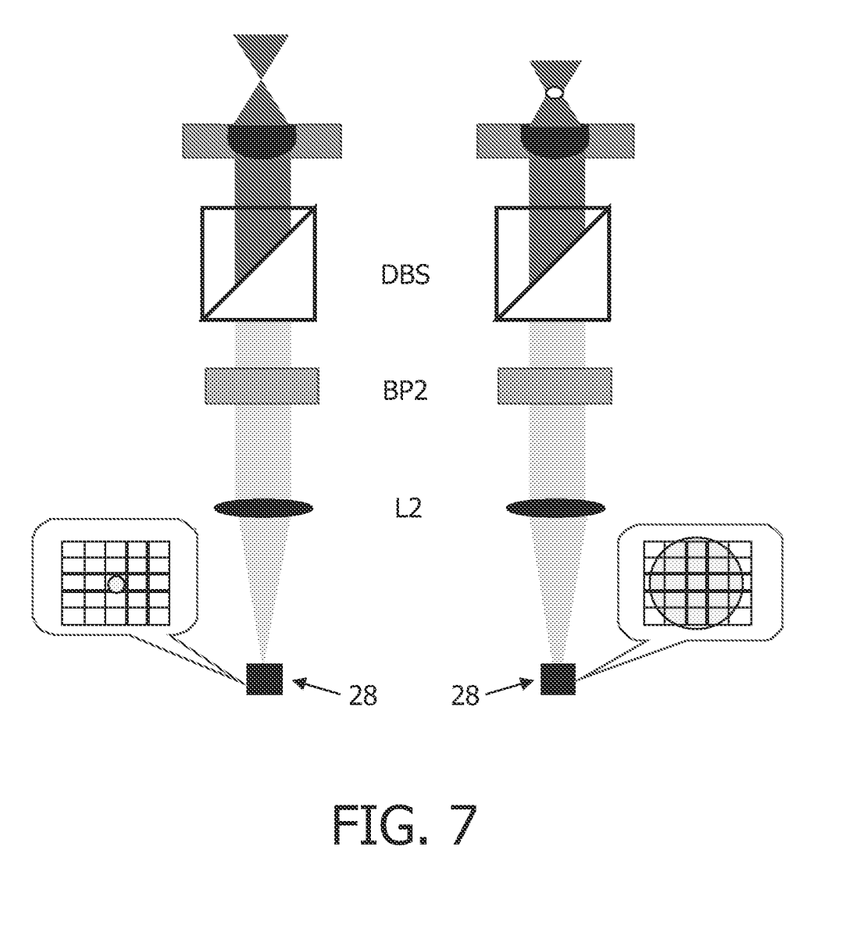
FIG. 7 shows a first example of detector arrangement which can be used in the apparatus of FIG. 2.

A first way to implement this is by using a large area pixilated detector, as shown in FIG. 7. This enables large volume detection, in conjunction with large area excitation. In a large volume detection mode, the fluorescence light reaches the detector and creates a significant signal in many or all of the pixels of the detector. Ideally the size of the detector corresponds to the size of the excitation volume (taking account of the optical scaling factors).

The system can be switched seamlessly to a confocal imaging mode. As the excitation light forms a tight focus in the sample volume, fluorescence light reaches only a limited number of detector pixels. This method is particularly attractive because no alignment is needed; the confocal area of interest in the detector plane can be determined post measurement via signal processing or can be known in advance based on system calibration. The imaging optics can be chosen such that the confocal volume is not imaged in the detector plane as much smaller than a detector pixel.

The left part of FIG. 7 shows the system in confocal imaging mode, with diffraction limited focus, and the right part of FIG. 7 shows the system in large area imaging mode, with aberration dominated focus.

Figure 8:
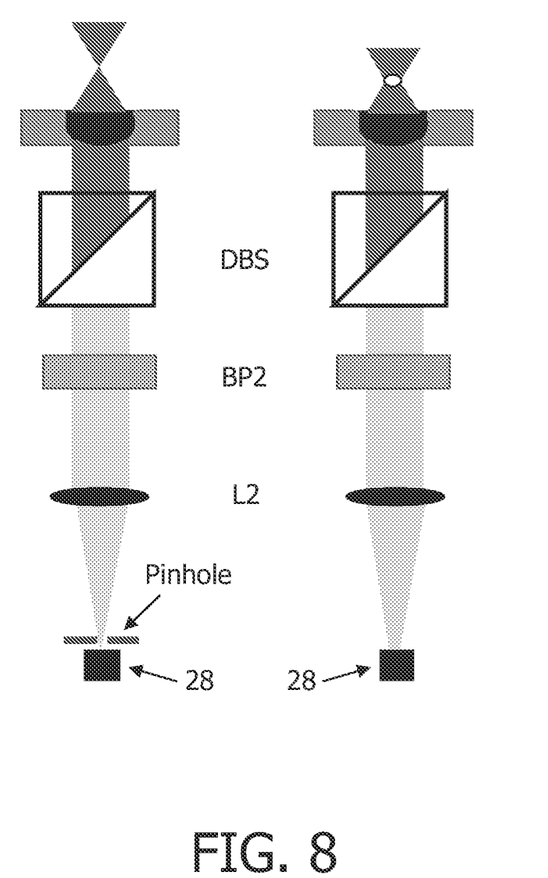
FIG. 8 shows a second example of detector arrangement which can be used in the apparatus of FIG. 2.

A large area detector may be preferred, for example to simplify the detection in the large volume detection mode. By "large area detector" is meant a detector with a single light receiving surface, in which the detector cannot distinguish between signals received at different parts of the surface. An example of this approach is shown in FIG. 8. In this design, the system can switch into confocal mode imaging by placing a pinhole 80 in front of the detector. The size and the position of the pinhole have to be confocal with the focus point of the excitation/collection lens.

The left part of FIG. 8 shows the system in confocal imaging mode, with diffraction limited focus and using the pinhole (or other aperture arrangement), and the right part of FIG. 8 shows the system in large area imaging mode, with aberration dominated focus.

Instead of a mechanical pinhole 80, an electrical shutter can be used which can be switched on and off and/or the diameter of which can be tuned.

Figure 9:
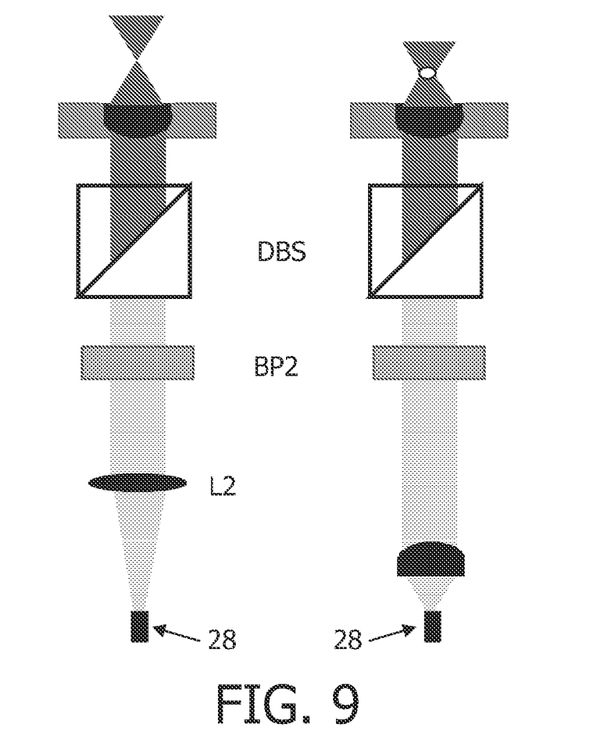
FIG. 9 shows a third example of detector arrangement which can be used in the apparatus of FIG. 2.

The focal length ratio between the imaging and collection lens determines the magnification of the object/image. As the detector size is fixed, it is possible to switch between confocal imaging to wide volume imaging by changing the imaging lens L2 in front of the detector. An example of this approach is shown in FIG. 9.

Ideally, for large volume detection the lens should be in front of the detector corresponding to the collection lens arrangement. In this way, many aberration terms are cancelled due to the symmetry of the system, and the effective imaging field is maximized. Optimally, the size of the detector is matched with the one of the lenses field. This is shown in the right part of FIG. 9.

To switch the system to confocal imaging mode, the lens in front of the detector can be exchanged for one that provides a large magnification (i.e. having a long focal length), so the tight focus spot excited in by the excitation/collection lens is imaged on the full detector size. In this way, the full detector area is used for light collection in both modes.

There are other ways to change the focal waist to those described above. For example, the focal waist can be increased on purpose by introducing a diffractive or refractive optical element or switching the properties of such an element in the excitation light path.

The non-confocal mode of operation of the device of the invention can be used to address the issue of slow speed of measurement. One major limitation of present q-PCR instruments is the still low speed. A typical amplification requires 30 to 40 cycles, each of them lasting approximately 1 minute. For point-of-care applications, half an hour is too long. Therefore it is important to speed up the processes. There are two limitations in the speed at the moment, i.e. the cycle time, which is limited by the heat transfer for heating and cooling and the number of cycles, which is limited by the sensitivity of the detection. Reducing the size of the device can improve the heat transfer but will reduce the sensitivity as well. Therefore a detection technology is required which allows the miniaturization of the device while increasing the sensitivity.

A first measure is to combine a high numerical aperture (NA) collection of fluorescence signal with efficient sampling of the PCR reaction volume. The sensitivity of the detection scales with $NA^2$. Typical NAs at present are 0.1 or less, but this can be increased to 0.65 or higher. This leads to an increase by a factor of 40 in the amount of collected fluorescence light.

Figure 10:
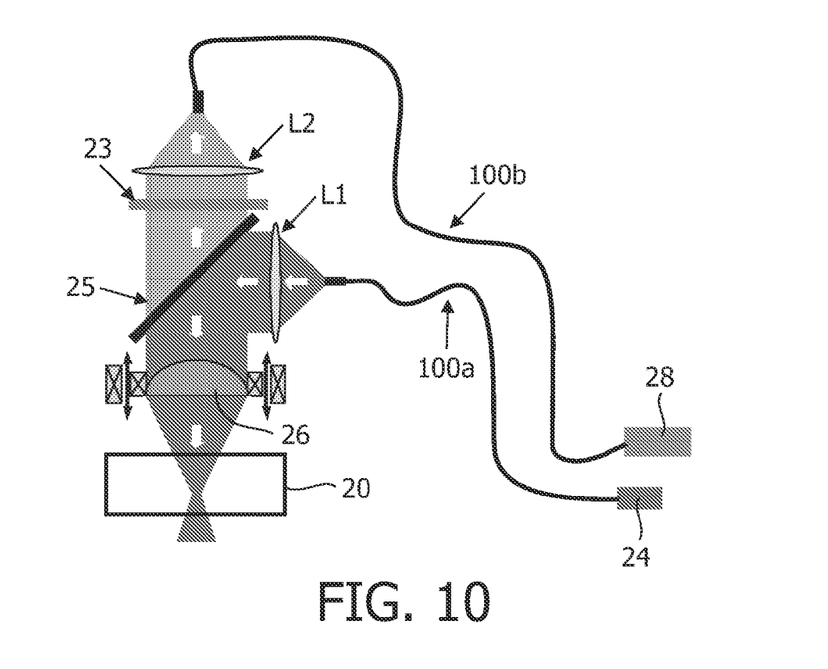
FIG. 10 shows another example of PCR apparatus of the invention.

FIG. 10 shows the use of multi-mode optical fibers for the excitation light and for the light provided to the detector. The components corresponding to those in FIG. 2 have been given the same reference numbers, and a description is not repeated. The system differs in that optical fibers 100a and 100b are provided at the output of the laser 24 and at the input to the detector 28. As explained above, the light coming out of the multi-mode optical fiber is not a point source but has a finite size, given by the fiber core. This has the effect that the light cannot be perfectly collimated and it is subsequently focused by the excitation/collection lens into a finite size spot. Ideally the fiber core dimensions are chosen such that the spot generated in the focal plane of the excitation/collection lens 26 is comparable with the field of view of this lens.

An advantage of having the excitation light brought in by a fiber 100a and delivering the collected fluorescence to the detector also by a fiber 100b is that the excitation/collection unit can be built small and robust and it can be easily scanned over an array of PCR reaction chambers.

Alternatively, an LED (light emitting diode) can be used as an excitation source. In a first embodiment, it can simply replace the laser and be collimated into the fiber, and subsequently collimated as it emerges from the other end of the fiber. In another embodiment, the LED can be placed directly in the focal plane of the collimator lens L1. This is possible because the LED is not a point source but the light is emitted from a finite surface, of the order of 100 µm×100 µm or larger. In this case, the active area of the LED would be ideally matched with the field of view of the excitation/collection lens 26 (divided by the ratio of the focal length of the collimator and excitation/collection lenses L1,26).

The collection/excitation lens 26 can be mounted in an actuator that allows a vertical scan of the lens. Using vertical only actuation, the excitation spot travels through the PCR chamber and efficiently excites a cylindrical volume, while at the same time it collects the excited fluorescence and it directs it to the detector via the collection optical fiber. The total fluorescence detected during a vertical scan is proportional with the amount of labeled DNA. Ideally, the scanned volume represents a significant fraction of the PCR volume. This is achieved by matching the focal size as closely as possible to the area of the chamber.

The lens 26 can have a focal depth which is smaller than the depth of the chamber. The vertical scanning can be used to identify the walls of the chamber.

Depending on the geometry of the PCR volume, a lateral scan can instead be the preferred embodiment to probe the PCR volume (or at least a significant fraction of it). Of course, a combination of a vertical and lateral scan can also be used to sample the PCR chamber.

The lateral dimension of the collection volume (for efficient fluorescence collection) is given by the field of view of the excitation/collection lens 26, which is ideally matched with the core of the excitation fiber and focal length of excitation/collection lens 26 and collimation lens L1.

Ideally:

$$d_{exc} \approx \frac{f_{exc/col}}{f_{collimator}} \cdot d_{fiber},$$

with:
dexc the diameter of the excitation spot in the lateral dimension;
fexc/col the focal length of the excitation/collection lens 26;
f collimator the focal length of the collimator lens L1;
dfiber the diameter of the excitation fiber 100a.

It is important that the light is scanned efficiently through the PCR volume, without producing a real focus that would give rise to bleaching of the fluorophore labels. Bleaching should be avoided by dynamically monitoring of the fluorescence during several PCR cycles.

The excitation/collection lens has a high NA and is light and small, for example with typical dimensions in the range of 5 mm. Even for a very simple lens design, small diameter and high NA, the field of view can be in the range of 50 microns diameter.

By matching the core of the fiber 100b that collects the fluorescence light to the field of view of the excitation/collection lens 26 and the focal length ratio of the two lenses 26,L1, a quasi-confocal filtering situation is realized. This makes the fluorescence detection less prone to stray light and unwanted fluorescence background excited elsewhere than in the PCR volume, (for example the auto fluorescence of the material that confines the PCR volume).

In the case of a light lens, for example of a few grams, a typical actuator (for example as used in the optical pick up unit "OPU" of a DVD player) can allow a vertical scan of 1 millimeter in tens of milliseconds or faster. The fluorescence acquisition, namely the sampling per PCR chamber, can take place in one vertical scan or in multiple vertical scans, and can be completed in the time scale of tens of milliseconds. This is more than sufficient since the time needed for a PCR cycle is in the order of tens of seconds or longer. The only requirement is that the fluorescence acquisition scan is synchronized with the relevant part of the PCR cycle, when the fluorophores are active, usually the end of the PCR cycle.

Preferably, if a large array of PCR chambers is to be scanned, the scanning of the OPU is synchronized with the temperature cycling of the array. Ideally the OPU can reach each PCR chamber at the right moment of the thermal cycle. In this way, a complete scan of the array can be extended over a time interval comparable with the time of a PCR cycle, (tens of seconds) without adding any extra delay due to the scanning (both lateral and vertical).

A typical minimum input volume for PCR amplification is in the range of few nano-liters, given by the initial concentration of the DNA to be amplified. A nano-liter is a volume of $106$ $\mu m3$ and at pico-molar concentration of active labels (typical concentration after few amplification steps) a nano-liter would contain $103$ fluorophores, and their excited fluorescence signal is easily detectable with the method described herein (where a significant fraction of the PCR volume is probed).

As mentioned above, the device can be used with multiple light sources and multiple filter arrangements to allow simultaneous monitoring of the luminescence of different fluorophores. The objective lens can have a high numerical aperture that allows a very efficient collection of the luminescence as well as a strong confinement of the excitation in the case of confocal readout, which enables a strong surface selectivity.

The measurement of the luminescence can be synchronized with reaction processes going on inside the analytical device, for instance induced by temperature changes, etc.

The fluorescence intensity can be probed in a multitude of reaction volumes by sequentially jumping to different wells. Identification codes can be incorporated in the wells that can be read out by the same excitation beam to render the coordinates of the corresponding luminescence intensity. The same locations can be measured multiple times to derive a time dependent behavior in the analytical solution.

The preferred applications of the invention are in the field of molecular diagnostics: clinical diagnostics, point-of-care diagnostics, advanced bio-molecular diagnostic research—biosensors, in particular related to DNA detection in combination with amplification methods, such as PCR, q-PCR, etc.

The preferred application of the invention is thus in molecular diagnostics based on the detection of nucleic acids after amplification, combining real time detection during amplification (rt-PCR) with amplification followed by immobilization by hybridization to capture probes (endpoint detection) in a single device. The device can select between the two techniques merely by using different chemicals on the cartridge and adjusting the control of the instrument, controllable by operator via software on the instrument.

The device can be used for scanning large arrays of hybridization spots as well as a multitude of reaction chambers for amplification by a combined x,y-high resolution actuation of the lens which transmits the excitation and luminescence radiation, combined with a fast stepping actuation mode.

The system can provide a high sensitivity and high spatial resolution based on a high numerical aperture of the focusing lens which ensures an efficient collection of the luminescence emitted by the labels attached to the oligonucleotides. The invention enables a high flexibility for molecular diagnostics and cost efficient solution for any degree of multiplexing and miniaturization of the reaction volumes, which makes it especially well suited for (micro-fluidics) compact integrated devices.

In the examples above, the system is used for fluorescence detection. However, the invention more generally relates more generally to the excitation of a sample and the detection of resulting light. This excitation can simply comprise illumination, and the induced luminescence is then reflection. Thus "excitation" should be understood to include illumination, and "light resulting from the excitation" should be understood to include reflection. The induced luminescence can also comprise phosphorescence.

In the examples above, a dichroic beam splitter DBS is used, as the preferred solution. However a normal (non-dichroic) beam splitter can be used as well, although some excitation power as well as collected fluorescence would be wasted.

The above-mentioned embodiments illustrate rather than limit the invention, and at that those skilled in the art will be able to design many alternative embodiments without departing from the scope of the appended claims.

For example, although not drawn, the system as explained above may be modified to have a focusing arrangement that is separate from a collection arrangement. Those skilled in the art will be able to add a standard collection arrangement to a focusing arrangement according tot the invention. The arrangements may be still have substantially the same design, but not share any elements. Alternatively, less elements may be shared than explained in the embodiments above.

In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the device claim enumerating several means, several of these means may be embodied by one and the same item of hardware. The mere fact that certain measures are recited in mutually different dependent claims does not indicate that the combination of these measures cannot be used to advantage.

The invention claimed is:

1. A detection system, comprising:
   a radiation source for providing input radiation;
   a radiation focusing arrangement for providing the input radiation to an analysis region of a sample;
   a radiation collection arrangement for collecting output radiation from the analysis region of the sample resulting from interaction of the input radiation with the sample;
   a radiation detector for detecting the collected output radiation; and
   operating means for operating the detection system in a first detection mode and a second detection mode, wherein in the first detection mode the analysis region has a first size and/or shape and wherein in the second detection mode the analysis region has a second size and/or shape that is different from the first size and/or shape, wherein the operating means is configured to modify the input radiation excitation path and the output radiation detection path of the system to implement the mode change,
   wherein a modification of the input radiation excitation path and the output radiation detection path of the system includes an introduction or a removal of an aberration to the input radiation between the radiation source and the analysis region as operated in the first detection mode.

2. The detection system as claimed in claim 1, wherein the operating means provide the analysis region with a first analysis area in the first detection mode and a second analysis area which is larger than the first analysis area in the second detection mode.

3. The detection system as claimed in claim 1 further comprising confocal imaging means for providing confocal detection to at least one of the first and second detection modes.

4. The detection system as claimed in claim 1, wherein the operating means provide the analysis region with a first analysis volume thickness in the first detection mode and a second analysis volume thickness in the second detection mode.

5. The detection system as claimed in claim 1, wherein the operating means comprise means for scanning a sample in the z-direction.

6. The detection system as claimed in claim 1, wherein the operating means comprise means for altering the focal depth of the radiation focusing arrangement.

7. The detection system as claimed in claim 1, further comprising a collimating refractive element for collimating the output of the radiation source, and wherein the operating means comprise means for moving the collimating refractive element relative to the radiation source and means for altering the focal depth of the radiation focusing arrangement.

8. The detection system as claimed in claim 1, wherein the operating means comprise at least one of a radiation fiber and a scattering element, each insertable into the input radiation path between the radiation source and the analysis region for introducing the aberration to the input radiation between the radiation source and the analysis region.

9. The detection system as claimed in claim 1, further comprising:
   an optical fiber,
   wherein the operating means further comprise a collimating element arranged in the input radiation path between the optical fiber and the analysis region, and
   wherein the detection system further comprises an imaging element and a further optical fiber, the further optical fiber being insertable in the output radiation path between the imaging element and the radiation detector.

10. The detection system as claimed in claim 1, further comprising a refractive element that is shared by the radiation focusing arrangement and the radiation collection arrangement and is arranged for providing the input radiation to the sample and for collecting the output radiation from the sample.

11. The detection system as claimed in claim 1, further comprising first and second imaging lens arrangements, such that the detector is operable in a first area mode in combination with the first detection mode and a second area mode in combination with the second detection mode.

12. The detection system as claimed in claim 1, wherein the radiation detector comprises spatially distributed pixels for detecting the radiation.

13. The detection system as claimed in claim 1, wherein the radiation detector comprises a single detector surface, and the detection system further comprises a detector aperture, such that the radiation detector is operable in a first area mode in combination with the first detection mode and a second area mode in combination with the second detection mode by adjusting the detector aperture.

14. The detection system as claimed in claim 1, wherein a modification of the input radiation excitation path and the output radiation detection path includes altering a focal depth of a common focal point of the input radiation excitation path and the output radiation detection path.

15. The detection system as claimed in claim 1, wherein a modification of the input radiation excitation path and the output radiation detection path includes altering a focal volume of a common focal point of the input radiation excitation path and the output radiation detection path.

16. A detection method for detecting output radiation from a sample, the detection method comprising the steps of:
   providing input radiation;
   focusing the input radiation thereby creating an analysis region on a sample;
   collecting output radiation from the analysis region of the sample resulting from interaction of the input radiation with the sample, and detecting the collected light; and
   varying the size and/or shape of the analysis region by modifying the input radiation excitation path and the output radiation detection path to implement a mode change, wherein a modification of the input radiation excitation path and the output radiation detection path of the system includes an introduction or a removal of an aberration to the input radiation between the radiation source and the analysis region as operated in the first detection mode.

17. The detection method as claimed in claim 16, wherein a modification of the input radiation excitation path and the output radiation detection path includes altering a focal depth of a common focal point of the input radiation excitation path and the output radiation detection path.

18. The detection method as claimed in claim 16, wherein a modification of the input radiation excitation path and the output radiation detection path includes altering a focal volume of a common focal point of the input radiation excitation path and the output radiation detection path.

* * * * *